United States Patent
Niemeläet al.

(10) Patent No.: US 6,910,674 B2
(45) Date of Patent: Jun. 28, 2005

(54) VALVE FOR USE IN A BREATHING APPARATUS

(75) Inventors: Tapani Niemelä, Mariefred (SE); Bruno Slettenmark, Järfälla (SE); Thomas Valeij, Huddinge (SE)

(73) Assignee: Maquet Critical Care AB, Solna (SE)

(*) Notice: Subject to any disclaimer, the term of this patent is extended or adjusted under 35 U.S.C. 154(b) by 204 days.

(21) Appl. No.: 10/268,517

(22) Filed: Oct. 9, 2002

(65) Prior Publication Data

US 2004/0069305 A1 Apr. 15, 2004

(51) Int. Cl.$^7$ ............................................. F16K 31/02
(52) U.S. Cl. ............................ 251/129.17; 251/129.19; 251/331
(58) Field of Search ........................ 251/129.17, 129.19, 251/331

(56) References Cited

U.S. PATENT DOCUMENTS

| | | | | |
|---|---|---|---|---|
| 3,429,552 A | * | 2/1969 | Huley et al. ............ | 251/129.17 |
| 4,699,137 A | * | 10/1987 | Schroeder ............... | 251/331 |
| 4,930,747 A | * | 6/1990 | Nakamura ............... | 251/129.17 |
| 5,265,843 A | * | 11/1993 | Kleinhappl ............. | 251/129.17 |
| 5,419,367 A | * | 5/1995 | Noya ..................... | 251/129.17 |
| 5,467,961 A | * | 11/1995 | Sausner et al. ........ | 251/129.15 |
| 5,630,403 A | * | 5/1997 | Van Kampen et al. .. | 251/129.17 |
| 5,947,155 A | * | 9/1999 | Miki et al. ............. | 251/129.1 |
| 6,019,344 A | * | 2/2000 | Engel et al. ............ | 251/129.01 |
| 6,722,629 B1 | * | 4/2004 | Nakazawa .............. | 251/129.19 |

FOREIGN PATENT DOCUMENTS

WO   WO 02/04850 A1 * 1/2002

* cited by examiner

*Primary Examiner*—John Bastianelli
(74) *Attorney, Agent, or Firm*—Schiff Hardin LLP

(57) ABSTRACT

A valve in a breathing device has a housing with an inlet and an outlet, a valve housing having an inlet and an outlet, a valve seat arranged in the housing, a valve body arranged in the housing to be freely moveable with respect to the valve seat between a closed position where the valve body completely covers the valve seat and an open position where the valve body is distanced from the valve seat. The valve body comprising a rigid central portion and a circumferential wrinkled and flexible portion devised for friction-free movement of the rigid central portion, and an actuator for controlling a force applied on the valve body in response to a control signal. The actuator includes an actuator body, a shaft having an end contactable with the valve body, and an electromagnetic displacement coil.

11 Claims, 5 Drawing Sheets

VALVE FOR USE IN A BREATHING APPARATUS

BACKGROUND OF THE INVENTION

1. Field of the Invention

The present invention relates to a valve of the type suitable for use in a breathing device.

2. Description of the Prior Art

Breathing devices such as medical ventilators and anesthetic apparatuses normally include an inspiratory side for supplying breathing gas toward a subject and an expiratory side for removing breathing gas from the subject.

In the inspiratory side, an inspiration valve is situated to control flow of gas and/or pressure in the inspiratory side. In the expiratory side, an expiration valve is situated to control flow of gas and/or pressure in the expiratory side.

Such valves can be controlled pneumatically, mechanically or electromechanically. Electromechanical actuators such as solenoids or voice coil motors have been used

SUMMARY OF THE INVENTION

An object of the invention is to provide a valve of the above type which is highly accurate, stable and reliable as well as practical, easy to maintain and support, and economical.

In a preferred embodiment of the invention, this object is achieved in a valve in a breathing device having a housing with an inlet and an outlet, a valve seat arranged in the housing, a valve body arranged in the housing that is freely moveable with respect to the valve seat between a closed position where the valve body completely covers the valve seat and an open position where the valve body is spaced from the valve seat. The valve body has a rigid central portion, a circumferential wrinkled and highly flexible portion which allows friction-free movement of the rigid central portion, and a soft portion on the rigid central portion facing the valve seat. An actuator is provided for controlling the force operating on the valve body relative to the valve seat in response to a control signal. The actuator includes a shaft attached to an electromagnetic displacement coil and having an enc contactable with the valve body.

The highly flexible portion of the valve body will not exercise any unwanted forces within its moving range. Ideally, the movement of the valve body will take place completely without friction or spring force action. In reality, a very small and almost constant spring force action will persist over the operational stroke. The highly flexible portion is made to ensure this. Structures similar to roll membranes can be employed.

Another important function of the highly flexible portion is to provide a highly effective gas seal against leakage from the gas flow path.

The overall construction of the valve is made to minimize or exclude friction forces from interfering with the operation of the valve. Basically, a linear correlation between the driving current and force exercised by the shaft on the valve body is present with the valve according to the invention. A given current I to the coil results in a force $F=k*I$ (where k is a constant) which is practically independent of the position of the shaft. Since the relationship $F=P*A$ (where P is pressure operating on the area A of the valve body) also exists, the valve opening will automatically adjust itself until the desired pressure P is achieved (linear relationship between current I and pressure P) independent of the magnitude of the gas flow through the valve. This results in a very accurate control over the pressure upstream of the valve body. When used as an expiration valve, the valve can exercise a precise control over the expiration pressure, etc.

This control also is enhanced by the fact that the valve body in all open positions will hover or float with respect to the valve seat. This effect is caused by allowing the valve body to freely tilt on the shaft end. In other words, the valve body strives to attain a fully equidistant position from the valve seat due to aerodynamic principles. When open, gas will flow out along the entire perimeter of the valve opening. No physical contact force between valve body and valve seat will therefore upset the desired balance ($F=k*I=P*A$). This promotes the accuracy and predictability of the valve control.

The separation of the actuator and valve body (or rather the entire housing) facilitates cleaning and selection of material. The separation also makes it easy to replace parts due to wear. Only the interior of the housing is exposed to the breathing gases and therefore requires proper disinfecting through autoclaving, washing etc. The actuator therefore can be designed entirely for its actuating purposes without requirements of being able to be autoclaved etc. The actuator may for instance be constructed to have a lifetime ten times longer than the valve body or more. Basically, this means that the actuator can remain the same and a number of housings are used (more or less) consecutively.

The two modular parts of housing and actuator can be separated and reassembled (in particular with different housings being exchanged on a regular basis). During normal exchanges (when the breathing device is not in use) the parts can be physically completely separated, which means there is no risk during separation and reassembly to interfere with alignment of shaft with respect of the valve body. In use however, there is a slight risk for a minute lateral displacement between the two modular parts. This could cause unwanted friction in the shaft movement when a standard bearing construction is used. This mainly is due to the presence of play within given tolerances between the parts.

To avoid this risk, the shaft can have a rounded end and be arranged in the actuator in a manner allowing the rounded end to be moved slightly in a lateral manner in addition to the axial movement. This can be achieved by using rounded or spherical bearings for the shaft or having part of the shaft display a slightly rounded area in contact with a sliding bearing.

At the same time the valve body can have a hole or recess in the rigid central portion, arranged so that the rounded end of the shaft will interact with the hole or recess. If a hole is used, it should be smaller than the diameter of the rounded end and if a recess is used it should have a radius larger that the radius of the rounded end of the shaft. This will ascertain a self-centering effect for the shaft-valve body arrangement that can accommodate any problems mentioned above.

The lateral deviation obtained will, due to the special bearing, not cause any friction so the control of the valve is not interfered with.

When the housing containing the valve body is removed for cleaning etc, the actuator will be completely exposed. Liquid or other material, however, is prevented from entering into the actuator body by means of a dome-shaped sealing between the rounded end and the actuator body interacting with a lip on the surface of the actuator body. This dome-shaped sealing is preferably free moving above the actuator body when the valve is activated, but seals around the lip when the shaft is maximally retracted (when the valve is inactivated, i.e. at zero current). The dome-shaped sealing diverts anything falling on it away from the shaft entrance of the valve body and the lip prevents any liquid persisting on the actuator body from entering same when the valve is activated and the dome-shaped sealing is raised from is sealing position. The placement of course carries the extra advantage that no friction is added during control of the valve since the dome-shaped sealing is not in physical contact with any other parts when the shaft is moving. (A similar sealing effect can be obtained by using bellows, but a bellows would always cause frictional hysteresis, so the innovative dome-shaped sealing is much more advantageous.)

Choice of materials is in some sense important. Both the shaft and the rigid portion (of the valve body) should be made of hard materials. However, the shaft preferably is harder than the rigid central portion of the valve body to ascertain that the shaft attains a higher durability. At the same time, the difference in hardness, as well as contact area (roundness of rounded end) must be chosen so the rigid central portion does not become indented by the contact pressure from the (rounded) end. A high surface finish also is important to reduce friction and facilitate movements between the shaft and the rigid portion when the shaft centers itself.

DESCRIPTION OF THE PREFERRED EMBODIMENTS

Figure 1:
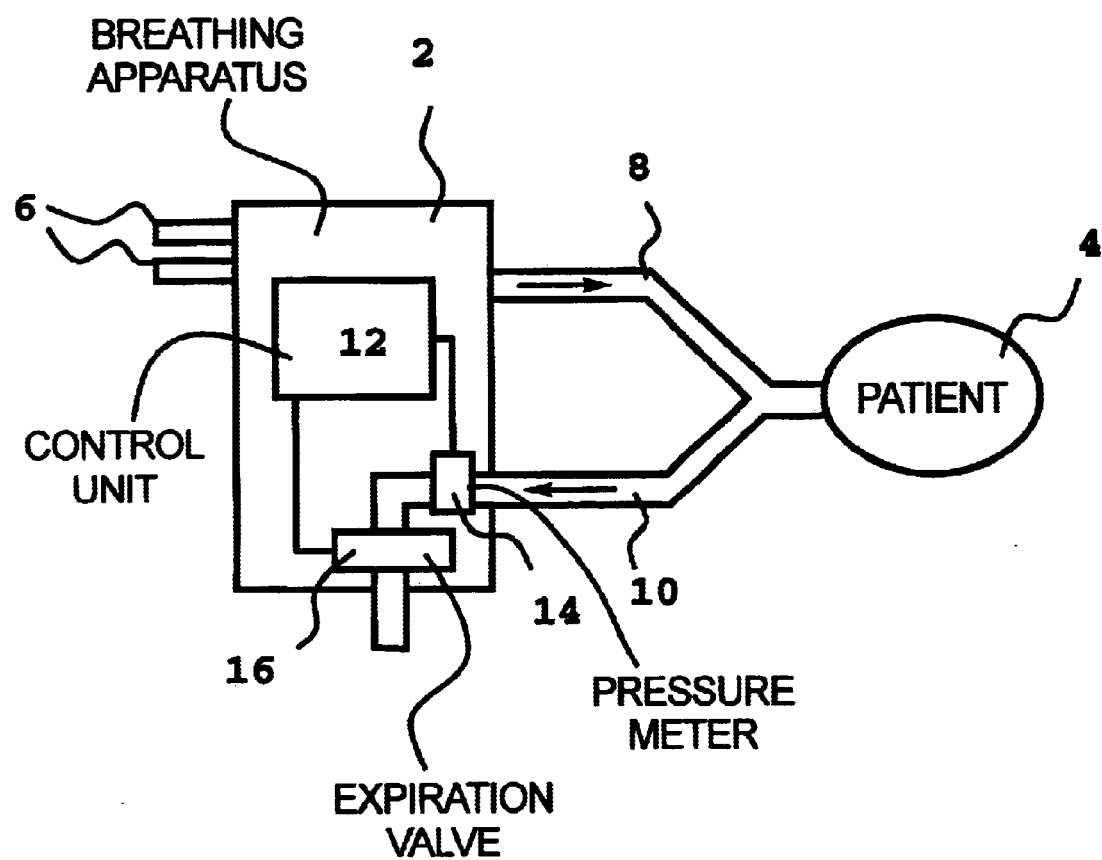
FIG. 1 schematically illustrates an example of a breathing apparatus in which an expiration valve according to the invention can be used.

A general overview of a breathing apparatus 2 connected to a patient 4 is depicted in FIG. 1. Gas can be supplied to the breathing apparatus 2 via gas inlets 6. From the breathing apparatus 2 breathing gas is transferred to the patient 4 via an inspiration tube 8 and from the patient 4 via an expiration tube 10.

The breathing apparatus 2 is controlled by a control unit 12. One example of a parameter that can be controlled is the positive end expiratory pressure, PEEP. A pressure meter 14 can measure pressure in the expiration tube 10 and forward a pressure signal to the control unit 12, which in turn sends a control signal to an expiration valve 16.

The present invention more particularly relates to the design of the expiration valve 16. The shown breathing machine 2 is thus only given as an example of working environment for the expiration valve 16. The breathing apparatus could be any known breathing apparatus, in particular any medical ventilator or anesthetic apparatus.

Figure 2:
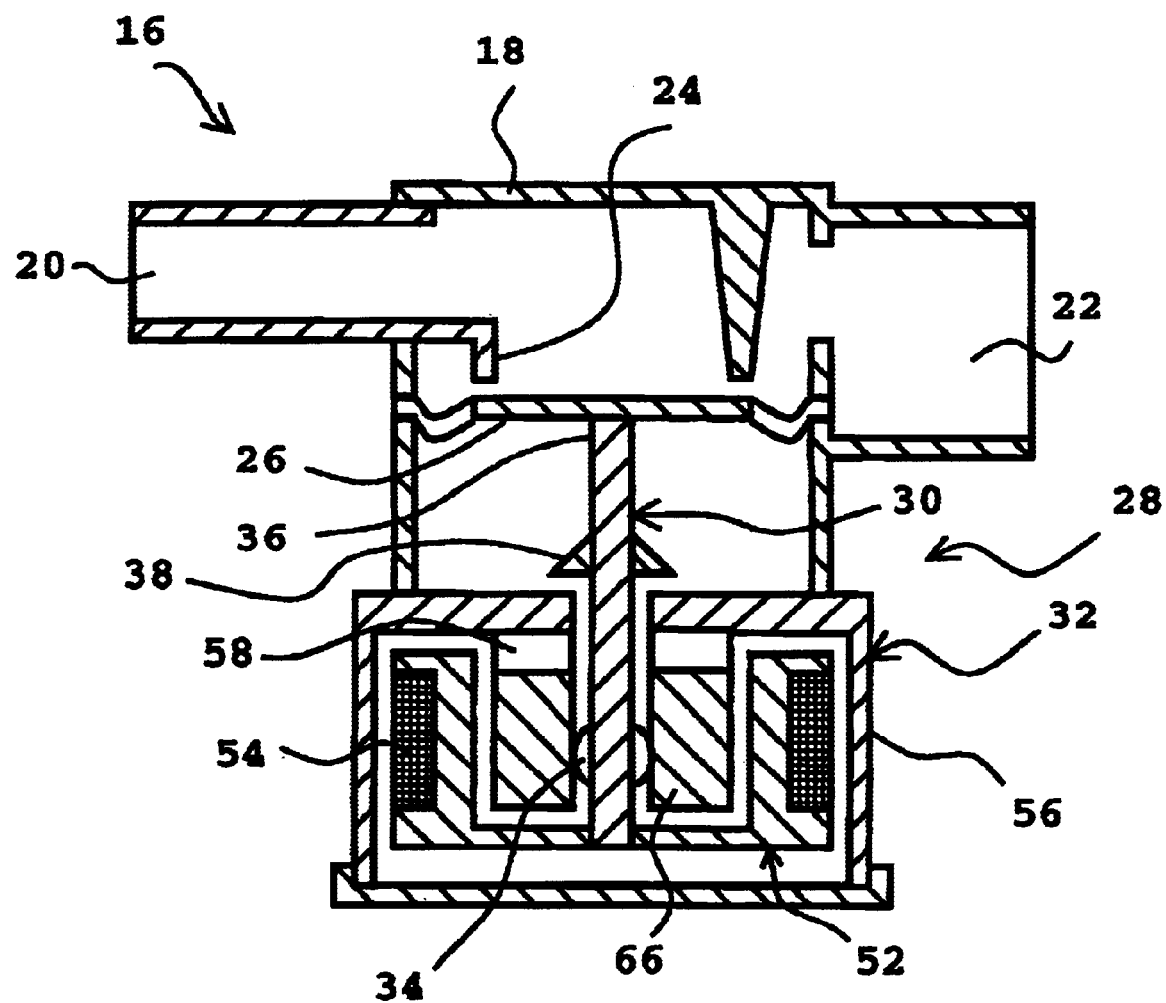
FIG. 2 shows an embodiment of the inventive expiration valve.

A preferred embodiment of the expiration valve 16 is shown in FIG. 2. The expiration valve 16 has a housing 18 with an inlet 20 and an outlet 22 for breathing gas.

A valve seat 24 and a valve body 26 are arranged in the housing 18 to interact with each other for control of a valve opening, i.e. distance between valve seat 24 and valve body 26.

An actuator 28 controls the force exercised on the valve body 26 toward the valve seat 24 depending on the control signal from the control unit 12 (FIG. 1). The pressure from the gas upstream the valve body (i.e. pressure in the expiration tube 10 in FIG. 1) constitutes a force in the opening direction of the valve 16. The balance between the two forces thus determines the opening of the valve in such way that the pressure is determined solely by the applied force and independent on the flow through the valve 16. By altering the force from the actuator 28, the pressure in the expiration tube can be controlled.

The actuator 28 has a shaft 30 attached to a displacement coil 52 inside an actuator body 32 and contactable with the valve body 26 for controlling the force with which the shaft 30 shall press on the valve body 26.

Since the shaft 30 is not attached to the valve body 26, only contactable therewith, the actuator 28 and the housing 18 can be completely separable. This has the distinct advantage that the parts exposed to breathing gas exhaled by the patient (housing 18) can be removed to be thoroughly cleaned and disinfected, whereas the more sensitive control parts of the actuator 28 such as the moving coil 52 and bearing 34 (that remain unexposed to contamination at all times) need not be exposed to such harsh treatment. Washing with a disinfecting cloth is normally sufficient for the actuator 28.

This further facilitates the possibility of having the housing 18 form an integral part of an expiratory cassette of the breathing machine. Such an expiratory cassette contains all expiratory components that require cleaning after each use or after a certain time. Such an expiratory cassette therefore can be removed easily and readily from the breathing machine for cleaning. The same or a new cassette then can be placed in the breathing apparatus.

The bearing 34 in the actuator body 32 preferably is rounded or spherical to make it possible for a first end 36 of the shaft 30 to move slightly in a lateral manner apart from the axial movements. More specifically in the preferred embodiment, the bearing 34 represents an interaction between a slight bulge (exaggerated in the figure) on the shaft 30 and a sliding bearing.

The lateral movement helps the expiration valve 16 to take up vibrations and jolts without affecting the operation of the valve. It also facilitates alignment of shaft 30 and valve body 26 when the shaft 30 is activated. The function of this is explained in more detail in connection with FIG. 3 below.

Also present on the shaft is a dome-shaped seal 38, which prevents water and other liquids or solids from entering the interior of the actuator body 32. This occurs in particular when the housing 18 with valve body 26 is removed for cleaning or replacement, which exposes the actuator 28. This will also be discussed in more detail with reference to FIG. 3 below.

Figure 3:
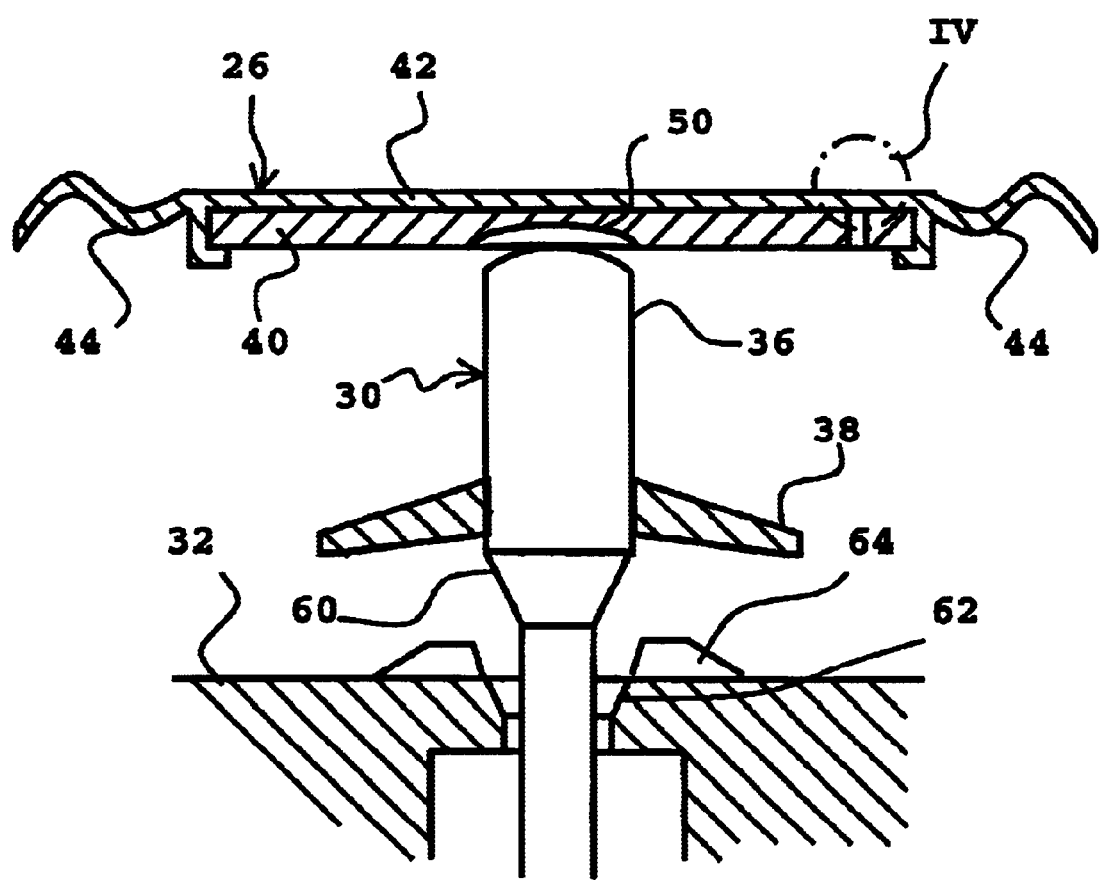
FIG. 3 shows in more detail how a valve body and actuator of the expiration valve in FIG. 2 are designed.

Certain parts of the preferred embodiment of the expiration valve 16 are shown in more detail in FIG. 3.

Here, it can be seen that the valve body 26 has a rigid central portion 40, facing the shaft 30, a soft portion 42 on the rigid central portion 40, facing the valve seat, and a circumferential wrinkled and highly flexible portion 44. The circumferential wrinkled and highly flexible portion 44 preferably would provide no additional axial force, but any force added is practically constant over the range of movement for the circumferential wrinkled and highly flexible portion 44. No force added means that the force from the actuator via shaft 30 will be directly correlatable with the desired pressure upstream the valve (F=P*A, where F is the force from the shaft, P is the desired pressure and A is the valve area exposed to the pressure). With a constant force added, compensation has to be done for the additional force (i.e. the above relation becomes F-c=P*A, where c represents the additional constant force). The flexible portion 44 also strives to maintain the central portion 40 (i.e. valve body 26) centered over the valve seat. The flexible portion also seals a part of the housing, providing a gas tight seal which ascertains that gas will only flow out through the outlet. A further advantageous effect of the flexible portion 44 is the provision of friction-free movement.

The friction-free movement is important because it creates an essentially linear relationship with no, or very low hysteresis between control current to the moving coil and closing pressure of the valve (F=k*I, where F is the force acting on the valve body, I is the control current and k is a constant. This enhances and facilitates control of the valve and allows for very high accuracy and performance. (With the force c above being close to zero F=P*A=k*I, which means a practically direct relationship between control current I and pressure P.)

In this specific embodiment, the soft portion 42 and the circumferential wrinkled and flexible portion 44 are formed by one single membrane. They may, however, also be formed by two or more separate components.

Figure 4:
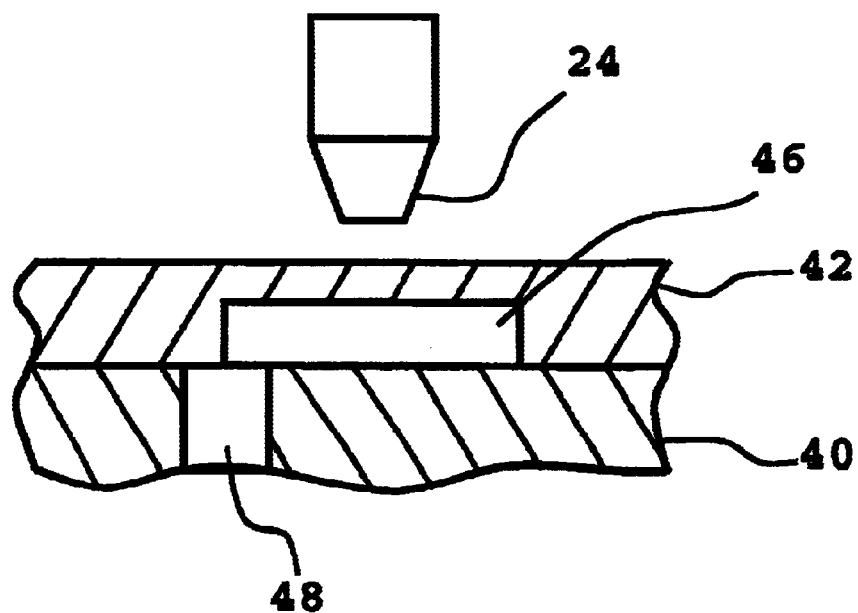
FIG. 4 is an enlargement of a section of the valve body in FIG. 3.

Another advantageous detail is indicated at IV and shown more clearly in FIG. 4. Here it can be seen that the soft portion 42 has a cutout 46. This cutout 46 is annular and situated in the contact area with the valve seat 24 (although having a width noticeably larger than the valve seat 24). The cutout 46 faces the portion 40, thereby forming a much thinner membrane facing the valve seat 24. This thinner membrane has several important implications. The valve can be closed completely with considerably lower force (without risk for leakage), the requirements for flatness of the valve seat 24 and tolerances for membrane surface on valve body 26 become much lower and there will be no physical contact between the membrane and the valve seat 24 even at very small openings (low flows) due to combination of membrane resilience, rounded end 36 of shaft 30 and aerodynamic physical principles and thus the force balance will not be disturbed.

A hole 48 (which could be a multitude of holes situated equidistantly from the center) is disposed in the central portion 40. This hole 48 (or holes) provide a major advantage. The hole 48 serves to release gas from the cutout 46 whenever the pressure changes within the cutout 48 (in relation to surrounding pressure). This can occur when the volume of the cutout 46 decreases as it engages the valve seat. This can also occur when exposed to higher temperatures or vacuum during disinfecting processes (autoclaving etc). The hole 48 (or holes) also will reduce the weight of the central portion 40, without altering its rigidity.

Figure 5:
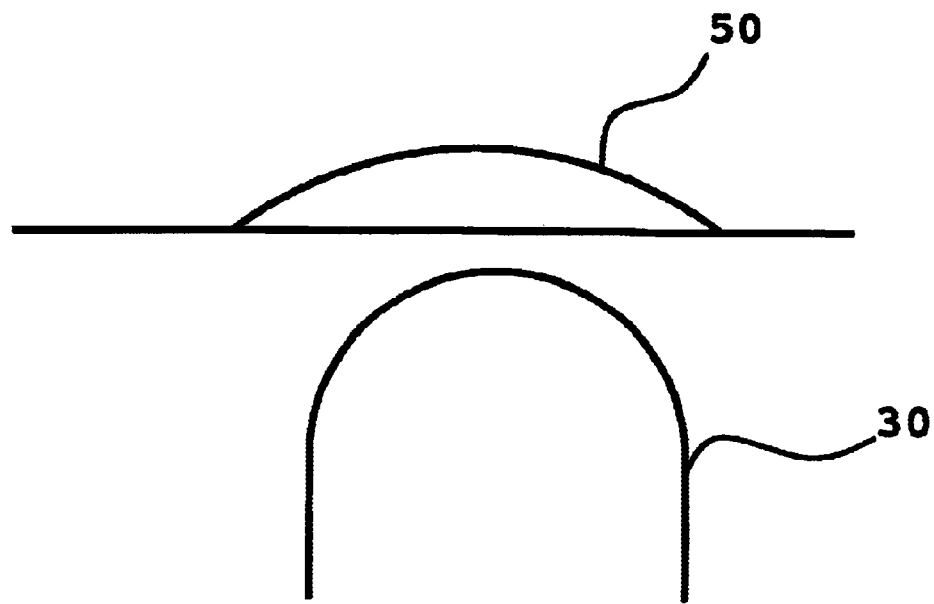
FIG. 5 shows a detail of how the shaft and valve body can be constructed for proper interaction in accordance with the invention.

Returning to FIG. 3, the interaction between the shaft 30 and valve body 26 will now be explained in detail. When the shaft 30 is in its lowest position (at zero current—not shown) it will not be in contact with the valve body 26. The valve body 26 will be suspended by the flexible portion 44. As the actuator 28 is activated, the shaft 30 moves to make contact with the valve body 26. For an exact force balance F=P*A, it is essential that the shaft 30 contacts the valve body 26 very close to it center and that the valve body 26 freely can tilt around the shaft. The shaft 30 therefore is rounded at the end 36 and a recess 50 is made in the center of the valve body 26. The recess 50 has a radius that is larger than the radius of the rounded end 36, which is evident from FIG. 5. This causes the shaft 30 and rigid portion 40 to make contact at a point, around which the valve body 26 can tilt.

As the shaft 30 makes contact with the valve body 26, the rounded end 36 will be guided into the recess 50. As explained previously, the end 36 can move in a lateral manner so the shaft 30 will assume a position with a small contact area in the center of the valve body 26. This also functions as a type of bearing, preventing any risk that the shaft will laterally move so much that it comes in contact with any other part of the actuator body 32 that the bearing described in connection with FIG. 2 above. There will thus be no additional friction forces present.

As mentioned, the dimensioning radius of the shaft's 30 rounded end 36 is important. Some of the purposes or functions it fulfils are to guide the shaft 30 to the center of the valve body, to minimize sliding and rolling friction between shaft 30 and valve body 26, to allow the valve body 26 to roll or tilt sufficiently to attain its floating position in relation to the valve seat, and to stabilize the valve body 26 in such floating position and not cause any mechanical damage on the valve seat 26.

The floating of the valve body 26 in relation to the valve seat is due aerodynamic effects as well as to geometric effects. The aerodynamic effects are basically such that as the pressure of the gas acts on the valve seat 26, any slant of the valve body in relation to the valve seat 26 will result in returning moment due to static and dynamic pressure relations, bringing the valve body 26 back to a planar position.

The geometric effects are basically such that should the valve body 26 roll slightly on the tip of the shaft 30 and become slanted, the new contact point will be off center. Thus a uniform pressure acting on the valve body 26 will cause a restoring moment, tending to stabilize the valve body 26 in a position where the moment is zero, i.e. where the contact point is exactly centered.

It is therefore beneficial to have contact surfaces made with a high smoothness, so that rolling and movements in the contact area between the shaft 30 and the valve body 26 results in a minimum of friction.

The recess 50 can be replaced by a hole (of less diameter than the shaft) in the central portion 40 without altering the effect or functionality. Further alternatives will be presented below.

The recess 50 (or hole) also serves as a mass reducer for the rigid central portion 40, without effecting the rigidity of it (similar to the hole or holes 48 mentioned in connection with FIG. 4).

The dome-shaped seal 38 also is shown in FIG. 3. Here it can be seen that the dome-shaped seal 38 can interact with a circular lip 64 at the central part of the actuator body 32. When the shaft 30 is completely retracted into the actuator body 32, the dome-shaped seal 38 will completely cover the lip 64, thereby completely sealing the interior of the actuator body 32. When the shaft 30 is raised (valve active), the lip 64 prevents any remaining or collecting amount of liquid to flow into the interior of the actuator body 32.

Further in FIG. 3, it can be seen that the shaft 30 has a tapered portion 60 that interacts with a correspondingly shaped recess 62 in the actuator body 32 as the shaft 30 is retracted into the actuator body 32. This assures that the shaft 30 is always properly centered when the valve is activated (at start up of the breathing machine, after change of expiration cassette (including valve body 26), etc.).

Another feature of the expiration valve 16 is evident from FIG. 2. The actuator body 32 has a moving part 52 with a winding 54 (the shaft 30 is also attached to, connected to or formed as an integral part of the moving part 52) and magnetically coupled to a core 56 with a permanent magnet 58, magnetized in the direction of the shaft 30.

The winding 54 and interior part 66 of the core 56 should be arranged to face each other. All parts of the core 56 except the permanent magnet 58 preferably are made of a ferromagnetically soft material, e.g. soft iron. The permanent magnet 58 preferably is placed in connection with the interior part 66 of the core 56 so that the magnetic field will be able to attain an essentially radial orientation across the winding 34 and bobbin part.

If the bobbin part of the moving part 52 is made of a highly conductive material such as Cu, Al, Ag, etc., eddy currents will be induced in the bobbin when it moves in the radial magnetic field resulting in a viscous damping, i.e. a damping force proportional to the velocity of the moving part 52. This is highly desirable in many applications.

This overall design thus creates damping, it has a linear relationship between current and force, it exhibits very little magnetic hysteresis since it operates at a constant magnetic working point and friction is kept low since there are only very small lateral forces involved. Therefore, the shaft 30 will move easily and predictably in the actuator body 32 and the entire actuator 28 is controllable through current only to provide a desired force, linear in current and with a desired damping characteristic.

Alternate embodiments can readily be arrived at by those skilled in the art. A few variations of possible alternatives in arranging the contact between the shaft and valve body are shown in FIGS. 6A and 6B.

Figure 6A:
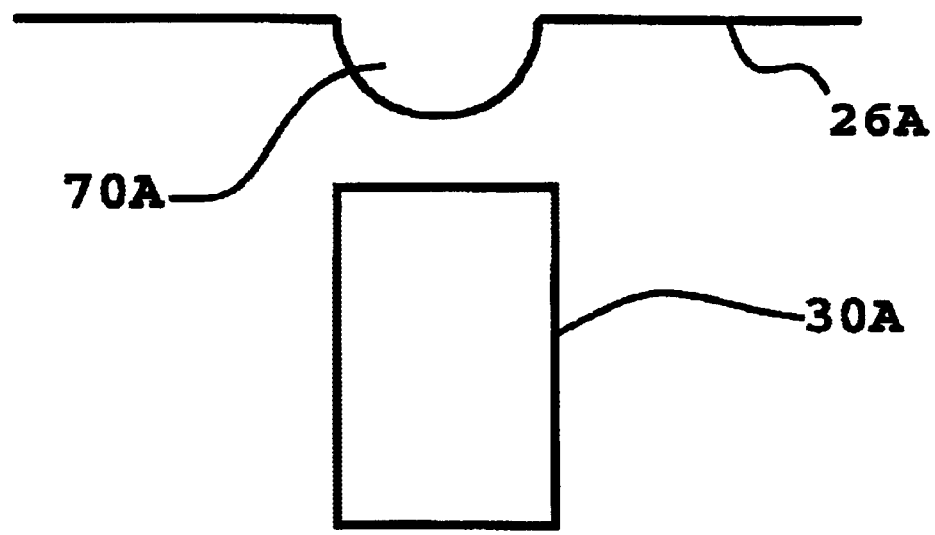
FIGS. 6A and 6B shows further examples of how shaft and valve body can be constructed for proper interaction.

As shown in FIG. 6A, the valve body 26A may have a rounded part 70A which can interact with a flat surface on a shaft 30A. This provides the same effects for tilting and providing geometric and aerodynamic effects striving to maintain a floating position for the valve body 26A in relation to the valve seat.

Figure 6B:
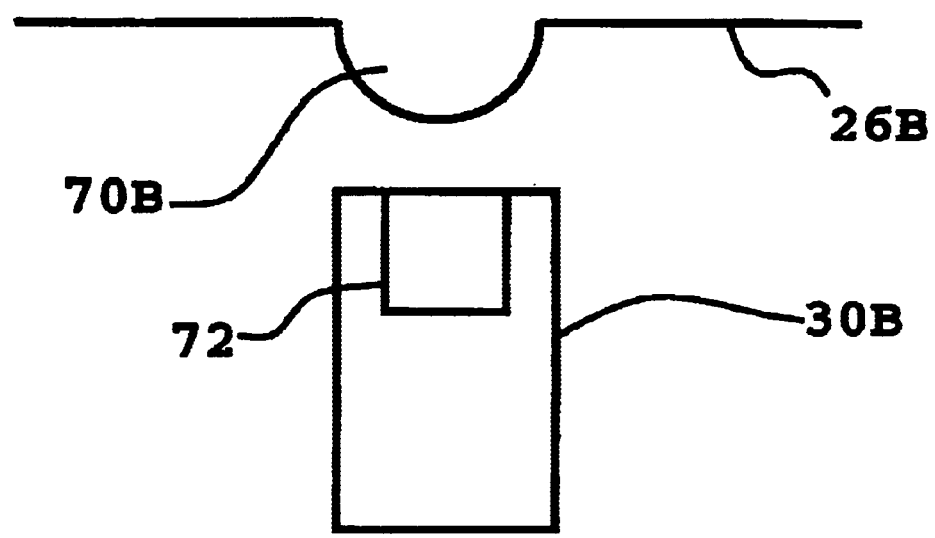

Likewise, in FIG. 6B the valve body 26B has a rounded part 70B interacting with a bore 72 in the shaft 30B for producing the same effect.

Although modifications and changes may be suggested by those skilled in the art, it is the intention of the inventors to embody within the patent warranted hereon all changes and modifications as reasonably and properly come within the scope of their contribution to the art.

We claim as our invention:

1. A valve comprising:

a housing having an inlet and an outlet adapted for a fluid flow;

a valve seat disposed in said housing in a path of said fluid flow, said valve seat having a surface with a surface diameter;

a valve body having a central rigid, substantially non-deformable, substantially flat portion and a circumferential, wrinkled and flexible portion disposed substantially parallel to said rigid portion and mounting said valve body in said housing so as to be freely movable relative to said valve seat and allowing friction-free movement of said rigid central portion, said valve body being disposed for interaction with said fluid flow and being movable between a closed position wherein said valve body completely covers said valve seat and an open position wherein said valve body is spaced from said valve seat said valve body comprising a soft portion on said rigid central portion facing said valve seat and having an annular cutout corresponding to said surface diameter; and an actuator for applying and controlling a force acting on said valve body in response to a control signal, opposed to a force acting on said valve body by interaction with said fluid flow, said actuator having an actuator body, a shaft having an end contactable with said valve body, and an electromagnetic displacement coil disposed in said actuator body for displacing said shaft, in response to said control signal, toward and away from said valve body.

2. A valve as claimed in claim 1 further comprising a mounting arrangement for mounting said shaft in said actuator body allowing said end of said shaft to move axially and laterally.

3. A valve as claimed in claim 2 wherein said mounting arrangement is a spherical bearing disposed within said displacement coil.

4. A valve as claimed in claim 2 wherein said mounting arrangement comprises a rounded bulge on said shaft and a slide bearing in said actuator body interacting with said rounded bulge.

5. A valve as claimed in claim 1 wherein said shaft has a tapered portion and wherein said actuator body has a tapered counterpart to said tapered portion interacting with said tapered portion, for automatically centering said shaft as said shaft is withdrawn into said actuator body away from said valve body.

6. A valve as claimed in claim 1 wherein said end of said shaft is rounded, and wherein said rigid central portion of said valve body has a rounded recess interacting with said rounded end of said shaft.

7. A valve as claimed in claim 1 wherein said end of said shaft is rounded, and wherein said rigid central portion of said valve body has a rounded hole interacting with said rounded end of said shaft.

8. A valve as claimed in claim 1 comprising a dome-shaped seal attached to said shaft between said actuator body and said end of said shaft.

9. A valve as claimed in claim 8 wherein said actuator body comprises a lip disposed to interact with said dome-shaped seal.

10. A valve as claimed in claim 1 wherein said shaft is comprised of a first material and wherein said rigid central portion of said valve body is comprised of a second material, said first material being harder then said second material.

11. A valve as claimed in claim 1 wherein said electromagnetic displacement coil and said actuator body are disposed relative to each other to electromagnetically damp axial movement of said shaft.

* * * * *